United States Patent [19]

König et al.

[11] Patent Number: 4,755,591

[45] Date of Patent: Jul. 5, 1988

[54] PROCESS FOR THE PREPARATION OF PEPTIDES BY USE OF PERCHLORATES

[75] Inventors: Wolfgang König; Volker Teetz, both of Hofheim am Taunus, Fed. Rep. of Germany

[73] Assignee: Hoechst Aktiengesellschaft, Fed. Rep. of Germany

[21] Appl. No.: 935,758

[22] Filed: Nov. 28, 1986

[30] Foreign Application Priority Data

Nov. 30, 1985 [DE] Fed. Rep. of Germany ....... 3542442

[51] Int. Cl.$^4$ ............................ C07K 1/02; C07K 1/06
[52] U.S. Cl. .................................... 530/309; 530/338; 530/339
[58] Field of Search ........................ 530/309, 338, 339

[56] References Cited

PUBLICATIONS

Journal of the Chemical Society, 19 (1983) 1060–62.
Berichte der Deutschen Chemi. Ges. (1926), vol. 59, 448–455.

*Primary Examiner*—Delbert R. Phillips
*Attorney, Agent, or Firm*—Finnegan, Henderson, Farabow, Garrett and Dunner

[57] ABSTRACT

The invention relates to a process for the preparation of protected arginine-containing peptides by fragment coupling, at least one arginine-containing fragment being reacted as perchlorate, and to protected secretin derivatives of the formula I described.

9 Claims, No Drawings

PROCESS FOR THE PREPARATION OF PEPTIDES BY USE OF PERCHLORATES

The invention relates to a process for the preparation of protected arginine-containing peptides by fragment coupling, which comprises in each fragment coupling at least one arginine-containing fragment being reacted as perchlorate.

Possible arginine-containing fragments within the meaning of the present invention are:

1. arginine whose COOH or $\alpha$-NH$_2$ group is optionally protected by a protective group customary in peptide chemistry, or
2. segments which contain arginine and other amino acids and whose functional group(s) is(are) optionally protected by (a) protective group(s) customary in peptide chemistry. Examples of suitable protective groups are described in Schröder, Lëbke, The Peptides, Volume I, Academic Press, New York 1965, pages 3–75 and 137–270.

The fragment coupling is carried out by standard processes such as are described in, for example, Perspectives in Peptide Chemistry, edited by Eberle et al., Karger, Basel 1981, pages 15–155. Coupling in the presence of carbodiimides, such as N,N'-dicyclohexylcarbodiimide; N,N'-di-tert.-butylcarbodiimide; N,N'-diisopropylcarbodiimide; N-ethyl-N'-(3-dimethylaminopropyl)carbodiimide or N,N'-bis-(4-nitrophenyl)carbodiimide, are preferred, where appropriate with the addition of N-hydroxysuccinimide, 1-hydroxybenzotriazole, 3-hydroxy-4-oxo-3,4-dihydro-1,2,3-benzotriazine or other racemization-reducing compounds. The coupling can be carried out both "classically" in solution as well as by the solid phase method (Merrifield) with a fragment which is covalently bonded to a resin during the course of the synthesis.

The use of higher peptides which are protected in the side chains as intermediates in peptide synthesis is frequently impeded by their poor solubility. These peptides are often so insoluble that further synthesis is out of the question. The poor solubility increases the reaction time and reduces the yield. These difficulties occur in the synthesis of, for example, secretin.

Secretin, a hormone from the duodenum, is a heptacosapeptide of the formula

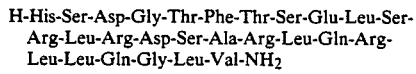

(Eur. J. Biochem. 15, 1970, pages 513–519). Secretin stimulates bicarbonate production by the pancreas and inhibits gastric acid secretion stimulated by gastrin.

Secretin has already been synthesized stepwise by use of the p-nitrophenyl ester method (J. Am. Chem.Soc. 89, 1967, pages 6753–6757) and the Repetitive Excess Mixed Anhydride (REMA) method (Helv. Chim. Acta 59, 1976, pages 1112–1126). The use of segments for the synthesis of secretin demands coupling methods which are as free of racemization as possible. Thus, by use of the azide method (J. Am. Chem. Soc. 90, 1968, pages 4711–4715) and the dicyclohexylcarbodiimide/N-hydroxysuccinimide (DCC/ HONSu) method (Chem. Ber. 105, 1972, pages 2508–2514) secretin has already been synthesized. Other variants of DCC coupling comprised the use of the racemization-reducing and solubilizing additions of 1-hydroxybenzotriazole (HOBt) and 3-hydroxy-4-oxo-3,4-dihydro-1,2,3-benzotriazine (HOObt) (Chem. Ber. 107, 1974, pages 215–231; Gut Hormones, ed. S. R. Bloom, 1978, pages 165–168). A solid phase synthesis of secretin has been described in Int. J. Peptide Protein Res. 9, 1977, pages 63–70.

The greatest difficulty in the abovementioned segment couplings is caused by the sparing solubility of the which, because of the high dilution of the reactants, make long reaction times and excesses of the N-terminal fragment necessary. It is true that it is possible to reduce somewhat the reaction time and, usually, also the reaction volume by preactivation of the N-terminal fragments with DCC/HOObt (Gut Hormones, ed. S. R. Bloom, 1978, pages 165–168). However, great difficulties also arise with the elimination of the benzyloxycarbonyl group (Z), which is used for intermediate amino protection, by catalytic hydrogenation. This is also mainly caused by the sparing solubility. Since acetic acid as solvent should be avoided where possible (acetic acid can be removed from basic peptides only with difficulty, and it causes acetylation of the amino groups during fragment coupling), it has already been necessary to change to costly solvents such as, for example, trifluoroethanol (Gut Hormones, ed. S. R. Bloom, 1978, page 167).

Surprisingly, the synthesis of protected arginine-containing peptides by coupling of the, frequently sparingly soluble, fragments is considerably facilitated if, in the coupling by the process according to the invention, at least one peptide component is used as perchlorate. The solubility of perchlorates of basic peptides in polar solvents, such as, for example, dimethylformamide or dimethylacetamide, is excellent, which is very advantageous for further reactions and improves the space yield. Reagents suitable for introducing the perchlorate are not only perchloric acid but also perchlorates of suitable amines, preferably pyridinium perchlorate which, in contrast to perchloric acid which contains water, can be weighed out anhydrous (Ber. dtsch. chem. Ges. 59, pages 448–455 (1926)).

The perchlorate ion binds to the strongly basic guanidino group, and the pyridine which is liberated goes into the solvent. Thus, it is possible by addition of pyridinium perchlorate to increase greatly the solubility, and hence to induce the reaction, of arginine-containing peptides. For example, the extremely sparingly soluble Z-Thr(Bu$^t$)-Ser(Bu$^t$)-Glu(OBu$^t$)-Leu-Ser(Bu$^t$)-Arg-Leu-OH can, with the addition of pyridinium perchlorate, be preactivated with DCC and HOObt in dimethylacetamide. Moreover, arginine, which is virtually insoluble in organic solvents, can be acylated with the addition of pyridinium perchlorate. This was not possible with arginine hydrochloride.

The perchlorate ions are not only suitable for increasing the solubility but also protect the guanidino group from acylation. Thus, pyridinium perchlorate has proven to be a very good additive for the protonation of the guanidino group in solid phase synthesis using Fmoc-amino acids, whereas hydrochloric acid is known not to be suitable for this purpose (see E. Atherton, R. C. Sheppard and D. Wade, J. Chem. Soc., Chem. Commun. 1983, 1060–1062).

A preferred process for the preparation of a protected secretin derivative of the formula I

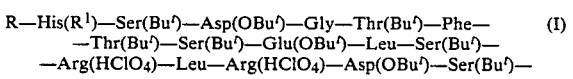

-continued
—Ala—Arg(HClO4)—Leu—Gln—Arg(HClO4)—Leu—Leu—
—Gln—Gly—Leu—Val—NH2, in which R and R$^1$ denote the Boc radical or (b) R denotes the Boc radical, and R$^1$ denotes hydrogen or (c) R and R$^1$ denote the adamantyloxycarbonyl radical, comprises reaction of a peptide of the general formula IIa H-X-Leu-Leu-Gln-Gly-Leu-Val-NH$_2$     (IIa)

in which X denotes
-Arg(HClO4)-,
-Arg(HClO4)-Leu-Gln-Arg(HClO4)-,
-Arg(HClO4)-Asp(OBu$^t$)-Ser(Bu$^t$)-Ala-Arg(HClO4)-Leu-Gln-Arg(HClO4) or
-Thr(Bu$^t$)-Ser(Bu$^t$)-Glu(OBu$^t$)-Leu-Ser(Bu$^t$)-Arg(HClO4)-Leu-Arg(HClO4)-Asp(OBu$^t$)-Ser (Bu$^t$)-Ala-Arg(HClO4)-Leu-Gln-Arg-(HClO4)

with the addition of 3-hydroxy-4-oxo-3,4-dihydro-1,2,3-benzotriazine (HOObt) in a "one-pot process" with the appropriate peptides with free carboxyl groups in polar solvents such as, for example, dimethylacetamide, with dicyclohexylcarbodiimide and the necessary amounts of a tertiary base such as, for example, N-ethylmorpholine, and precipitation of the peptides, which have thus been synthesized, as perchlorates from water with the addition of appropriate amounts of perchloric acid and, where appropriate, of a perchlorate such as NaClO4.

The elimination by hydrogenolysis of the N$^\eta$-nitro protective group of arginine in perchloric acid is known from J. Amer. Chem. Soc. 101, 1979, pages 1569-1576.

A particularly preferred process comprises obtaining the abovementioned peptide of the formula IIa by hydrogenation of benzyloxycarbonyl-containing fragments of the general formula II Z-X-Leu-Leu-Gln-Gly-Leu-Val-NH$_2$     (II)

in which X denotes -Arg(Z$_2$)-, -Arg(Z$_2$)-Leu-Gln-Arg-(HClO4)-, -Arg(Z$_2$)-Asp(OBu$^t$)-Ser(Bu$^t$)-Ala-Arg(HJClO4)-Leu-Gln-Arg (HClO4)- or -Thr(Bu$^t$)-Ser(Bu$^t$)-Glu(OBu$^t$)-Leu -Ser(Bu$^t$)-Arg(HClO4)-Leu-Arg(HClO4)-Asp(OBu$^t$)-Ser (Bu$^t$)-Ala-Arg(HClO4)-Leu-Gln-Arg(HClO4)-, in dimethyl-acetamide with the addition of a palladium catalyst, the pH being maintained between 4 and 6 by addition of a solution containing perchloric acid, and further reaction of the latter in the manner described above. It is also possible to add equivalent amounts of pyridinium perchlorate if no autotitrator can be used. The solvent hitherto used for the hydrogenation of Z-Arg(Z$_2$)-Leu-Leu-Gln-Gly-Leu-Val-NH$_2$     (III)

was glacial acetic acid (Chem. Ber. 104, 1971, page 2441). About 350 ml of glacial acetic acid were used for 10 mmol of the substance. In order completely to remove the acetic acid, which is necessary in order to prevent acetylation in the next peptide-forming step, it is necessary to add at least two equivalents of HBr or HCl and then to carry out several reprecipitations, with the addition of pyridine, from methanol and ethyl acetate or diisopropyl ether. Thus, it would be more advantageous to carry out a catalytic hydrogenation in solvents such as methanol or dimethylacetamide with the addition of HCl or HBr. Attempts of this nature have failed owing to the sparing solubility of III in the abovementioned solvents. Nor did suspensions dissolve during the hydrogenation. Hence, it was surprising to find that III, which is virtually insoluble in dimethylacetamide, rapidly dissolves with the addition of perchloric acid during the catalytic hydrogenation, with the formation of H-Arg(HClO4)-Leu-Leu-Gln-Gly-Leu-Val-
NH$_2$HClO4     (IV)

Only 120 ml of dimethylacetamide are necessary for 10 mmol of III, that is to say about one third of the amount of acetic acid described above. Apart from the working up being more straightforward, the peptide diperchlorate IV thus obtained has the advantage of being more soluble in polar solvents, such as dimethylacetamide and dimethylformamide. For example, in the reaction of Z-Arg(Z$_2$)-Leu-Gln-OH with the corresponding peptide dihydrobromide (Chem. Ber. 104, 1971, pages 2443-2444) about 650 ml of dimethyl-formamide are used as solvent for 10 mmol, whereas a 10 mmol batch requires only 70 ml of dimethylacetamide, that is to say approximately one tenth of the solvent, with the peptide diperchlorate IV. This reduces the reaction time from 7 days to a few hours, and the space yield is substantially increased.

Similar observations are made with the other fragments as well. The process for the catalytic hydrogenation of Z-Arg(Z$_2$)-Leu-Gln-Arg(HClO4)-Leu-Leu-Gln-
Gly-Leu-Val-NH$_2$     (V)

to give

H-Arg(HClO4)-Leu-Gln-Arg(HClO4)-Leu-Leu-
Gln-Gly-Leu-Val-NH$_2$HClO4     (VI)

is as for III. About 220 ml of dimethylacetamide are required for 10 mmol, whereas the corresponding hydrobromide (Chem. Ber. 104, 1971, page 2444) requires 1540 ml of glacial acetic acid for 10 mmol.

In the condensation of 10 mmol of VI with Z-Arg(Z$_2$)-Asp-(OBu$^t$) -Ser(Bu$^t$)-Ala-OH, only 45 ml of dimethylacetamide are now used as solvent, whereas approximately the same batch with the corresponding decapeptide trihydrochloride still requires 70 ml of solvent (Gut Hormones, ed. S. R. Bloom, 1978, page 166). The catalytic hydrogenation of the tetradecapeptide thus obtained Z-Arg(Z$_2$)-Asp(OBu$^t$)-Ser(Bu$^t$)-Ala-Arg(HClO4)-
Leu-Gln-Arg(HClO4)-Leu
-Leu-Gln-Gly-Leu-Val-NH$_2$     (VII)

to give

H-Arg(HClO4)-Asp(OBu$^t$)-Ser(Bu$^t$)-Ala-Arg
HClO4)-Leu-Gln
-Arg(HClO4)-Leu-Leu-Gln-Gly-Leu-Val-NH$_2$
HClO4     (VIII)

in turn takes place without difficulty in dimethylacetin amide (10 mmol in 250 ml), whereas 10 mmol of the corresponding dihydrobromide have been hydrogenated in 2,000 ml of 80 per cent acetic acid (Chem. Ber. 104, 1971, page 2450) and the dihydrochloride has been hydrogenated in the costly trifluoroethanol (Gut Hormones, ed. S. R. Bloom, 1978, page 167).

The sparingly soluble

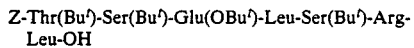
Z-Thr(Bu$^t$)-Ser(Bu$^t$)-Glu(OBu$^t$)-Leu-Ser(Bu$^t$)-Arg-Leu-OH readily dissolves in the presence of VIII, so that once more the condensation to give

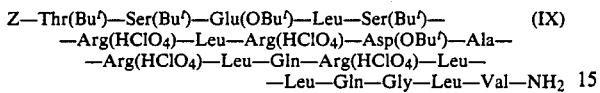
Z—Thr(Bu$^t$)—Ser(Bu$^t$)—Glu(OBu$^t$)—Leu—Ser(Bu$^t$)—    (IX)
—Arg(HClO$_4$)—Leu—Arg(HClO$_4$)—Asp(OBu$^t$)—Ala—
—Arg(HClO$_4$)—Leu—Gln—Arg(HClO$_4$)—Leu—
—Leu—Gln—Gly—Leu—Val—NH$_2$ in a "one-pot process" is possible in a small volume of solvent. A 10 mmol batch can readily be carried out in 200 ml of a dimethylformamide/dimethylacetamide mixture, whereas an analogous batch with the corresponding tetrahydrobromide required more than 500 ml of solvent (Chem. Ber. 107, 1974, page 230).

The catalytic hydrogenation of IX to give

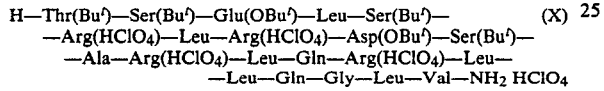
H—Thr(Bu$^t$)—Ser(Bu$^t$)—Glu(OBu$^t$)—Leu—Ser(Bu$^t$)—    (X)
—Arg(HClO$_4$)—Leu—Arg(HClO$_4$)—Asp(OBu$^t$)—Ser(Bu$^t$)—
—Ala—Arg(HClO$_4$)—Leu—Gln—Arg(HClO$_4$)—Leu—
—Leu—Gln—Gly—Leu—Val—NH$_2$ HClO$_4$ is possible in dimethylacetamide as with the benzyloxycarbonyl segments already described above. 1 g of the substance IX smoothly dissolves in 10 ml of dimethylacetamide. To dissolve 1 g of the corresponding tetrahydrobromide, about 140 ml of a 4:1 mixture of methanol and dimethylacetamide (Chem. Ber. 107, 1974, page 231) or about 270 ml of 80 per cent acetic acid (Chem. Ber. 105, 1972, page 2512) were required. The reaction of X with

Boc-His-Ser(Bu$^t$)-Asp(OBu$^t$)-Gly-Thr(Bu$^t$)-Phe-OH to give Ib requires about 40 ml of a mixture of dimethylformamide and dimethylacetamide (1:1) for each mmol. With the corresponding pentahydrobromide more than twice the amount of solvent is required (Chem. Ber. 107, 1974, page 231) and, when DCC/N-hydroxysuccinimide is used as condensing reagent, about five times the amount of solvent is needed (Chem. Ber. 105, 1972, page 2513).

The preferred solvent used for the catalytic hydrogenation of the benzyloxycarbonyl segments, which is carried out at pH 4 - 6 using an autotitrator, is dimethylacetamide, since perchloric acid solutions are more stable in dimethylacetamide than in dimethylformamide. The formyl radical is readily eliminated by perchloric acid with the formation of dimethylamine. Dimethylacetamide is also slowly attacked by perchloric acid. Thus, only freshly prepared perchloric acid/dimethylacetamide solutions should be used. Nevertheless, if water does not reduce the solubility too much, it is also possible to use aqueous perchloric acid (1-2 N) to titrate the amino groups which are being liberated. Once the hydrogenation is complete, the catalyst (Pd catalyst on charcoal or barium sulfate) is filtered off with suction, and the filtrate is concentrated. The residue can then be triturated with suitable solvents such as, for example, ethyl acetate or diisopropyl ether, there usually being the formation of amorphous precipitates which can be filtered off with suction. It is advisable to purify the products at the stage of peptide VI and VIII. The decapeptide triperchlorate VI can be very well purified by counter-current partition between n-butanol and water, whereas the tetradecapeptide tetraperchlorate VIII is purified by gel filtration on an isopropylated, cross-linked dextran gel in water as the eluent. In order to prevent bacterial growth on the column and in the eluate, Chloretone (1,1,1-trichloro- 2-methyl-2-propanol) is added to saturation. The Chloretone can be removed after the purification by extraction with ethyl acetate.

The working up after a segment coupling with DCC and HOObt is straightforward. Where possible, once the reaction is complete the precipitated dicyclohexylurea is filtered off with suction, and the Z-peptide perchlorate is precipitated with water with the addition of the calculated amount of perchloric acid. If the precipitated substance is difficult to filter, then addition of NaClO$_4$ converts the milky emulsion into a suspension which can readily be filtered.

The invention also relates to a peptide of the formula I in which R and R$^1$ have the meaning defined above.

EXAMPLE 1

H-Arg(HClO$_4$)-Leu-Leu-Gln-Gly-Leu-Val-NH$_2$
HClO$_4$ 22 g (18.2 mmol) of Z-Arg(Z$_2$)-Leu-Leu-Gln-Gly-Leu-Val-NH$_2$ are suspended in 220 ml of dimethylacetamide. After addition of Pd/charcoal catalyst, catalytic hydrogenation is carried out at pH 4.5 in an autotitrator with the addition of 1N HClO$_4$ in dimethylacetamide. (The 1N HClO$_4$ in dimethylacetamide should be prepared fresh each time, since perchloric acid slowly hydrolyzes dimethylacetamide to give dimethylamine and acetic acid.)

Preparation of approx. 1N HClO$_4$ in dimethylacetamide: 110 ml of 60 per cent HClO$_4$ are slowly added dropwise to 800 ml of stirred and efficiently cooled dimethylacetamide (highly exothermic reaction) and the solution is then made up to 1,000 ml with dimethylacetamide.

After the hydrogenation is complete, the catalyst is filtered off with suction, and the filtrate is concentrated to about 100 ml. The peptide is precipitated with 600 ml of ethyl acetate and is filtered off with suction. The peptide, which is very hygroscopic, is then stirred once more with 600 ml of ethyl acetate, filtered with suction and dried over P$_2$O$_5$ under high vacuum. Yield 18.2 g (92%), melting point: foams at 112°-124°, $[\alpha]_D^{20}$ = −30.7° (c=1, 80 per cent acetic acid). $^1$H-NMR spectrum: The two dimethylamide bands are seen at δ=2.7-2.9. The acetyl groups of dimethylacetamide and ethyl acetate are seen between δ=1.9 and 2.0.

Elemental analysis:
C$_{36}$H$_{68}$N$_{12}$O$_8$.2HClO$_4$.0.8 dimethylacetamide.1 H$_2$O (MW 1085.68): Calculated: C 43.37; H 7.35; Cl 6.53; N 16.51; H$_2$O 1.66. Found: C 43.3; H 7.1; Cl 6.5; N 16.1; H$_2$O 1.7.

EXAMPLE 2

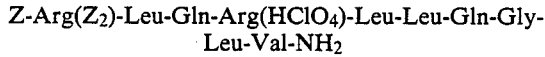
Z-Arg(Z$_2$)-Leu-Gln-Arg(HClO$_4$)-Leu-Leu-Gln-Gly-Leu-Val-NH$_2$ 12.24 g (15 mmol) of Z-Arg(Z$_2$)-Leu-Gln-OH (finely ground) are added to a stirred solution of 2.445 g (15 mmol) of 3-hydroxy-4-oxo-3,4-dihydro-1,2,3-benzotriazine (=HOObt) in 105 ml of dimethylacetamide at 40°

C.. Once everything has dissolved, the solution is allowed to reach room temperature and 16.93 g (15 mmol) of H-Arg-Leu-Leu-Gln-Gly-Leu-Val-NH$_2$ .2 HClO$_4$.1 H$_2$O 1.3 DMA are slowly added, with stirring. The mixture is stirred at room temperature until everything has dissolved. The solution is now cooled to 10° C. (starts to become viscous) and, with stirring, 1.95 ml (15 mmol) of N-ethylmorpholine and 3.9 g (18.9 mmol) of dicyclohexylcarbodiimide are added successively. The mixture is allowed to reach room temperature while stirring. Normally, the mixture becomes solid after about 4 hours. In a few cases the mixture remains stirrable until the next day. The mixture is left to stand at room temperature overnight and then stirred with a mixture of 600 ml of ice-water and 15 ml of 2N aqueous perchloric acid. The mixture is stirred in the cold for 15 minutes and filtered with suction. Water is used for washing. The precipitate is then stirred once more with 300 ml of water at room temperature for 1-2 hours. The precipitate is filtered off with suction and washed with water. It is dried to constant weight over P$_2$O$_5$.

Yield: 28 g (92%), melting point 222° C. (in other batches melting points of 240° C. or 253°-255° C. were also found). $[\alpha]_D^{20} = -27.1°$ (c=1, 80 per cent acetic acid) (angles of rotation from other batches: $-27.8°$, $-28.9°$ and $-27.4°$).

According to the working-up, the substance contains 1 mole-equivalent of dicyclohexylurea.

According to NMR, the substance contains 0.5 mole-equivalent of dimethylacetamide, and according to the Fischer water determination it contains 3 mole-equivalents of water.

Calculated molecular weight:

| | |
|---|---|
| Peptide perchlorate | 1697.40 |
| Dicyclohexylurea | 224.34 |
| 3 water | 54.048 |
| 0.5 dimethylacetamide | 43.562 |
| Total molecular weight | 2019.35 |

EXAMPLE 3

H-Arg(HClO$_4$)-Leu-Gln-Arg(HClO$_4$)-Leu-Leu-Gln-Gly-Leu-Val-NH$_2$. HClO$_4$ 27 g (13.37 mmol) of Z-Arg(Z$_2$)-Leu-Gln-Arg-Leu-Leu-Gln-Gly -Leu-Val-NH$_2$.HClO$_4$. DC-urea.3H$_2$O 0.5 dimethylacetamide are suspended in 300 ml of dimethylacetamide. After addition of Pd/charcoal catalyst, catalytic hydrogenation is carried out at pH 4.5 in an autotitrator with addition of freshly prepared 1N HClO$_4$ in dimethylacetamide. After the hydrogenation is complete, the catalyst is filtered off with suction, and the filtrate is concentrated to dryness under high vacuum. The residue is dissolved in 150 ml of aqueous 0.02 N HCl which is saturated with n-butanol. Insoluble constituents (mainly DC-urea) are removed by filtration, and then counter-current partition between 0.02 N HCl and n-butanol is carried out in 7 steps. The n-butanol phase should be saturated with 0.02 N HCl, and the 0.02 N HCl should be saturated with n-butanol. The individual steps are checked by TLC (TLC: n-butanol/pyridine/water/glacial acetic acid as 60/20/24/6). The satisfactory fractions (water 5-7 and n-butanol 4-7) are combined and concentrated under high vacuum. The residue is triturated with diisopropyl ether and filtered off with suction. The substance is initially very hygroscopic. This property is lost after drying over P$_2$O$_5$ in vacuo. Yield 15.15 g (main fraction). The side fractions (water 3-4 and n-butanol 2-3), which contain considerable amounts of the desired peptide in addition to impurities, are concentrated separately and once more subjected to counter-current partition as above in phase amounts of 100 ml. The utilizable fractions (water 3-7 and n-butanol 7) are concentrated, triturated with diisopropyl ether, and the solid is filtered off with suction and dried over P$_2$O$_5$ under high vacuum. In order to remove the water which interferes, it is advisable also to carry out a distillation with toluene before the trituration with diisopropyl ether. Yield 5.45 g (2nd fraction). Overall yield 20.6 g (72%).

$[\alpha]_D^{20} - 27.6°$ (c=1, 80 per cent acetic acid).

According to NMR, the substance contains 6 mole-equivalents of dimethylacetamide, 0.75 mole-equivalents of diisopropyl ether, and according to Fischer water determination it contains 1.5 mole-equivalents of H$_2$O.

Calculated molecular weight:

| | |
|---|---|
| Decapeptide.3 HClO$_4$ | 1495.9 |
| 6 dimethylacetamide | 522.7 |
| 0.75 diisopropyl ether | 76.6 |
| 1.5 water | 27.6 |
| Total molecular weight: | 2122.8 |

EXAMPLE 4

Z-Arg(Z$_2$)-Asp(OBu$^t$)-Ser(Bu$^t$)-Ala-Arg(HClO$_4$)-Leu-Gln-Arg (HClO$_4$)-Leu-Leu-Gln-Gly-Leu-Val-NH$_2$ 8.73 g (9 mmol) of Z-Arg(Z$_2$)-Asp(OBu$^t$)-Ser(Bu$^t$)-Ala-OH. 0.5 H$_2$O and 1.47 g (9 mmol) of 3-hydroxy-4-oxo-3,4-di-hydro-1,2,3-benzotriazine (=HOObt) are dissolved in 45 ml of dimethylacetamide. While stirring, 19.1 g (9 mmol) of H-Arg-Leu-Gln-Arg-Leu-Leu-Gln-Gly-Leu-Val-NH$_2$.3HClO$_4$ (contains, according to NMR, 0.75 mole-equivalent of diisopropyl ether and 6 mole-equivalents of dimethylacetamide, together with 1.5 mole-equivalent of H$_2$O) are added and, on heating to 40° C., everything dissolves. The solution is then cooled to 0° C., and 2.34 ml (18 mmol) of N-ethyl-morpholine are added. The reaction solution should assume a yellow color during this (HOObt acts as indicator). If the color change does not occur, the decapeptide contains too much hydrochlorid acid originating from the counter-current partition and further N-ethylmorpholine is added carefully, until the color changes to yellow.(Excess N-ethylmorpholine must be avoided because of the risk of racemization). Then 2.34 g (11.26 mmol) of DCC are added, and the mixture is stirred at 0° C. for one hour and at room temperature for three hours. It is left to stand at room temperature overnight. Completeness of reaction checked by TLC in glacial acetic acid/n-butanol/water as 1:3:1.

The mixture solidifies to a gel-like mass which is triturated with 1,000 ml of water with the addition of 4.5 ml of 2N aqueous perchloric acid. The precipitate is filtered off with suction, thoroughly washed with water, and dried over P$_2$O$_5$ in vacuo.

Yield 22.9 g (99%). The substance contains 1 mole-equivalent of DC-urea. Melting point 194°-200° C. $[\alpha]_D^{20} = -22.6°$ (c=1, in 80 per cent acetic acid).

EXAMPLE 5

H-Arg(HClO$_4$)-Asp(OBu$^t$)-Ser(Bu$^t$)-Ala-Arg HClO$_4$)-Leu-Gln -Arg(HClO$_4$)-Leu-Leu-Gln-Gly-Leu-Val-NH$_2$. HClO$_4$ 37 g (14.4 mmol) of Z-Arg(Z$_2$)-Arg(OBu$^t$)-Ser(Bu$^t$)-Ala-Arg -Leu-Gln-Arg-Leu-Leu-Gln-Gly-Leu-Val-NH$_2$.2 HClO$_4$ (+DC-urea) are dissolved in 370 ml of dimethylacetamide. The solution remains cloudy. Without filtering, Pd catalyst is added, and hydrogenation is carried out at pH 4.5 in an autotitrator with the addition of freshly prepared 1N HClO$_4$ in dimethylacetamide or water. After the hydrogenation is complete, the catalyst is filtered off with suction, and the filtrate is concentrated. The residue is dissolved in 60 ml of water, and insolubles (mainly DC-urea) are removed by filtration. The filtrate is chromatographed on Sephadex LH 20. Water saturated with Chloretone is used as eluent (Chloretone acts as disinfectant and can easily be removed later).

Column dimensions: about 4 m long and 8 cm diameter. It is important to remove the ninhydrin-positive impurities (the main impurity was found to be H-Arg-Asp(OBu$^t$)-Ser (Bu$^t$)-Ala-OH). The eluate checked by TLC in n-butanol/pyridine/water/glacial acetic acid as 60:20:24:6. The peptide-containing eluate is extracted three times with ethyl acetate to remove the Chloretone and, after the ethyl acetate dissolved in the water has been removed by distillation, is freeze-dried. Yield 17.73 g (55%). $[\alpha]_D^{20} = -26.8°$ (c=1, in 80 per cent acetic acid). According to analysis, the substance is a hexahydrate. Elemental analysis: C$_{77}$H$_{146}$Cl$_4$N$_{26}$O$_{35}$.6 H$_2$O (2246.2):

Calculated: C 41.17; H 7.09; Cl 6.31; N 16.21; H$_2$O 4.82.

Found: C 41.3; H 7.1; Cl 6.4; N 16.0; H$_2$O 5.1.

EXAMPLE 6

Z-Thr(Bu$^t$)-Ser(Bu$^t$)-Glu(OBu$^t$)-Leu-Ser(Bu$^t$)-Arg(HClO$_4$)-Leu -Arg(HClO$_4$)-Asp(OBu$^t$)-Ser(Bu$^t$)-Ala-Arg(HClO$_4$)-Leu-Gln -Arg(HClO$_4$)-Leu-Leu-Gln-Gly-Leu-Val-NH$_2$ (a) 1.2 g (1 mmol) of Z-Thr(Bu$^t$)-Ser(Bu$^t$)-Glu(OBu$^t$)-Leu-Ser (Bu$^t$)-Arg-Leu-OH.2 H$_2$O and 163 mg (1 mmol) of 3-hydroxy-4-oxo-3,4-dihydro-1,2,3-benzotriazine (=HOObt) are suspended in a mixture of 10 ml of dimethylacetamide and 10 ml of dimethylformamide. To this are added, at room temperature, 2.24 g (1 mmol) of H-Arg-Asp (OBu$^t$)-Ser(Bu$^t$)-Ala-Arg-Leu-Gln-Arg-Leu-Leu-Gln-Gly-Leu -Val-NH$_2$.4 HClO$_4$.6 H$_2$O. Solution occurs during this. Now 0.26 ml (2 mmol) of N-ethylmorpholine and a solution of 440 mg (2.13 mmol) of dicyclohexylcarbodiimide (=DCC) in 5 ml of dimethylacetamide are added at room temperature. The mixture is left to stir at room temperature for about 4 hours and to stand at room temperature overnight. If possible (where the solution has not become gel-like), the next day the DC-urea is filtered off with suction, and the filtrate is stirred with 200 ml of water to which 1 ml of 2N HClO$_4$ (2 mmol) has previously been added. The peptide separates out in the form of an emulsion. The addition of 4 ml of a 50 per cent aqueous NaClO$_4$ solution results in a satisfactory flocculent precipitate of the peptide. It is filtered off with suction and washed with a little water.

Yield after drying over P$_2$O$_5$: 3.17 g (96.5%). $[\alpha]_D^{20} = -17.8°$ (c=1, in 80 per cent acetic acid).

(b) 90 mg (0.5 mmol) of pyridinium perchlorate and 81.5 mg (0.4 mmol) of HOObt are added to a suspension of 600 mg (0.5 mmol) of Z-Thr(Bu$^t$)-Ser(Bu$^t$)-Glu(OBu$^t$)-Leu-Ser (Bu$^t$)-Arg-Leu-OH.2 H$_2$O in 0.5 ml of dimethylacetamide. Once everything has dissolved, 412 mg (2 mmol) of DCC are added, and the mixture is left to stir at room temperature for two hours. In the meantime, 1.07 g (0.5 mmol) of H-Arg-Asp(OBu$^t$)-Ser(-Bu$^t$)-Ala-Arg-Leu-Gln-Arg -Leu-Leu-Gln-Gly-Leu-Val-NH$_2$.4 HClO$_4$.6 H$_2$O are dissolved in 5 ml of dimethylacetamide. The above mixture is sucked through a small filter into the latter solution, washing with a little dimethylacetamide, and 0.13 ml (1 mmol) of N-ethylmorpholine is added, and the mixture is left to stir at room temperature for 2 hours. The peptide is then precipitated by addition of 100 ml of water. The peptide is removed by centrifugation and is dried, Yield: 1.21 g.

EXAMPLE 7

H-Thr(Bu$^t$)-Ser(Bu$^t$)-Glu(OBu$^t$)-Leu-Ser(Bu$^t$)-Arg(HClO$_4$)-Leu -Arg(HClO$_4$)-Asp(OBu$^t$)-Ser(Bu$^t$)-Ala-Arg(HClO$_4$)-Leu-Gln -Arg(HClO$_4$)-Leu-Leu-Gln-Gly-Leu-Val-NH$_2$. HClO$_4$ 3.3 g (about 1 mmol) of protected Z-secretin(7-27)-heneicosapeptide tetraperchlorate (for formula, see above) are dissolved in 33 ml of dimethylacetamide, Pd/charcoal catalyst is added, and catalytic hydrogenation is carried out at pH 4.5 in an autotitrator with the addition of freshly prepared 1N HClO$_4$ in dimethylacetamide or water. After the reaction is complete, the catalyst is filtered off with suction, and the filtrate is concentrated under high vacuum. The residue is triturated with ethyl acetate and filtered off with suction.

Yield 3.17 g (97%).

$[\alpha]_D^{20} = -22.0°$ (c=1, in 80 per cent acetic acid).

EXAMPLE 8

Boc-His-Ser(Bu$^t$)-Asp(OBu$^t$)-Gly-Thr(Bu$^t$)-Phe-Thr(Bu$^t$)-Ser (Bu$^t$)-Glu(OBu$^t$)-Leu-Ser(Bu$^t$)-Leu-Ser(Bu$^t$)-Arg(HClO$_4$)-Leu -Arg(HClO$_4$)-Asp(OBu$^t$)-Ser(Bu$^t$)-Ala-Arg(HClO$_4$)-Leu-Gln -Arg(HClO$_4$)-Leu-Leu-Gln-Gly-Leu-Val-NH$_2$ 27.2 g (8.3 mmol) of H-Thr(Bu$^t$)-Ser(Bu$^t$)-Glu(OBut)-Leu-Ser(Bu$^t$)-Arg(HC104)-Leu -Arg(HC104)-Asp(OBut)-Ser(Bu$^t$)-Ala-ArgHClO$_4$)-Leu-Gln -Arg(HClO$_4$)-Leu-Leu-Gln-Gly-Leu-Val-NH$_2$.HClO$_4$ are added to a stirred solution of 9.51 g of Boc-His-Ser (Bu$^t$)-Asp(OBut)-Gly-Thr(Bu$^t$)-Phe-OH and 1.36 g of HOObt in 166 ml dimethylacetamide and 166 ml of dimethylformamide.

Once everything has dissolved, at 0° C. 2.2 ml of N-ethylmorpholine and 3.7 g of dicyclohexylcarbodiimide are added, and the mixture is stirred at 0° for one hour and at room temperature overnight. The next day, the solution is aspirated into a mixture of 1.3 liter of water, 8.3 ml of 2N HClO$_4$ and 42.5 ml of a 50 per cent NaClO$_4$ solution. The precipitate is filtered off with suction, washed with water and dried over P$_2$O$_5$ in vacuo.

Yield 32.9 g.

According to amino acid analysis the peptide content is about 80% (=83% yield).

$[\alpha]_D^{20} = -11.8°$ (c=1, in 80 per cent acetic acid).

EXAMPLE 9

(a) Fmoc-Leu-OObt 2.06 g of DCC are added, at 0° C., to a solution of 3.53 g of Fmoc-Leu-OH and 1.63 g of HOObt in 40 ml of methylene chloride. The mixture is stirred at 0° C. for 1 hour and left to stand at room temperature overnight. The precipitate is filtered off with suction, and the filtrate is concentrated. The residue is triturated twice with petroleum ether, filtered off with suction and dried in vacuo.

Yield 5.2 g, amorphous.

(b) Fmoc-Leu-Arg-OH 5 g of Fmoc-Leu-OObt are added to a suspension of 1.74 g of L-arginine, 1.63 g of HOObt and 1.8 g of pyridinium perchlorate in 20 ml of dimethylacetamide, and the mixture is stirred at room temperature. After 1 hour everything has dissolved. The solution is left to stand at room temperature overnight, and the next day it is concentrated. The residue is partitioned between 180 ml of pentanol and 160 ml of water (+20 ml of saturated aqueous NaHCO3 solution). This partition is followed by a 5-step countercurrent partition between 180 ml of pentanol and 180 ml of water each time. The fractions containing pure Fmoc-Leu-Arg-OH are concentrated, and the residue is triturated with ether.

Yield: 4.1 g, melting point 145°–155° C. with decomposition, $[\alpha]_D^{20} = -18.5°$ (c=1, in methanol).

EXAMPLE 10

H-Asn-Ser-Phe-Arg-Tyr-OH

The synthesis was carried out with an Applied Biosystems 430 A peptide synthesizer.

The peptide was synthesized on a p-benzyloxybenzyl alcohol resin ("Wang resin": S. Wang, J. Am. Chem. Soc. 95, 1328 (1973)), which was esterified with Fmoc-Tyr(Bu$^t$)-OH by a known method (E. Atherton et al., J. Chem. Soc. Chem. Comm. 1981, 336) (degree of substitution: 0.4 mequiv./g). 1 g of resin was used for the synthesis. 1 mmol of each of Fmoc-Asn-OH, Fmoc-Ser(Bu$^t$)-OH, Fmoc-Phe-OH and Fmoc-Arg-OH were weighed, together with 1.5–2.5 equivalents of HOBt, into the cartridges supplied by the manufacturer of the apparatus. In the case of the arginine derivative 1 equivalent of pyridinium perchlorate was added. The activation of the amino acid derivatives as HOBt esters was carried out in the cartridges by dissolving in 4 ml of dimethylformamide and then adding 2 ml of a 0.55 M solution of diisopropylcarbodiimide in dimethylformamide.

A typical synthesis cycle is listed below:
1. Elimination of the protective group with 2×8 ml of a 20 per cent solution of piperidine in dimethylformamide for 10 minutes each time.
2. Washing with dimethylformamide (6×8 ml).
3. Preloading of the resin with HOBt by treatment for 10 min with a 0.5 M solution of HOBt in dimethylformamide, followed by pumping off the solution.
4. Coupling for 25–45 min of the Fmoc-amino acid OBt ester which has been preactivated in the cartridge for 30–45 min.
5. Washing with dimethylformamide (6×8 ml).

After the synthesis is complete, first the Fmoc group is eliminated from the peptide-resin using 20 per cent piperidine in dimethylformamide, and then the peptide is cleaved off from a sample (100 mg) by treatment with trifluoroacetic acid/methylene chloride/phenol as 70:30:5 for two hours. The resin is filtered off and washed with cleavage solution, and the filtrate is concentrated in vacuo. The phenol is removed by stirring several times with ethyl acetate. The remaining crude peptide is dissolved in 10 per cent acetic acid, and the solution is filtered and freeze-dried.

Yield: 23.8 mg of crude peptide.

Amino acid analysis after hydrolysis in 6N HCl at 120° C.. for 24 hours: Asp (1.03), Ser (0.81), Tyr (0.89), Phe (1.00), Arg (0.88), no ornithine (ornithine is produced by acid hydrolysis of the arginine which is acylated on the guanidino group).

FAB mass spectrum: 686 (=molecular mass+H$^+$)

We claim:

1. A process for the preparation of protected arginine-containing peptides by fragment coupling, which comprises in each fragment coupling at least one arginine-containing fragment being reacted as perchlorate.

2. The process as claimed in claim 1, wherein an optionally protected arginine is reacted as perchlorate.

3. The process as claimed in claim 1, wherein an arginine-containing segment is reacted as perchlorate.

4. The process as claimed in claim 1, wherein one fragment is covalently bonded to a solid phase during the course of the synthesis.

5. The process as claimed in claim 1, wherein the coupling is carried out in the presence of a carbodiimide.

6. The process as claimed in claim 1, wherein the coupling is carried out in the presence of N,N'-diisopropylcarbodiimide or N,N'-dicyclohexylcarbodiimide, where appropriate with the addition of N-hydroxysuccinimide, 1-hydroxybenzotriazole, 3-hydroxy-4-oxo-3,4-dihydro-1,2,3-benzotriazine or other racemization-reducing compounds.

7. A process for the preparation of a protected secretin derivative of the formula I R—His(R$^1$)—Ser(Bu$^t$)—Asp(OBu$^t$)—Gly—Thr(Bu$^t$)—Phe— (I)
—Thr(Bu$^t$)—Ser—(Bu$^t$)—Glu(OBu$^t$)—Leu—Ser(Bu$^t$)—
—Arg(HClO$_4$)—Leu—Arg(HClO$_4$)—Asp(OBu$^t$)—Ser(Bu$^t$)—
—Ala—Arg(HClO$_4$)—Leu—Gln—Arg(HClO$_4$)—Leu—Leu—
—Gln—Gly—Leu—Val—NH$_2$ wherein
(a) R and R$^1$ denote the Boc radical or
(b) R denotes the Boc radical, and R$^1$ denotes hydrogen or
(c) R and R$^1$ denote the adamantyloxycarbonyl radical, which comprises reaction of a peptide of the general formula (IIa)

H-X-Leu-Gln-Gly-Leu-Val-NH$_2$ (IIa)

wherein X denotes
-Arg(HClO$_4$)-,
-Arg(HClO$_4$)-Leu-Gln-Arg-(HClO$_4$)-,
-Arg(HClO$_4$)-Asp(OBu$^t$)-Ser(Bu$^t$)-Ala-Arg(HClO$_4$)-Leu-Gln-Arg-(HClO$_4$)-or
-Thr(Bu$^t$)-Ser(Bu$^t$)-Glu(PBu$^t$)-Leu-Ser(Bu$^t$)-Arg HClO$_4$)-Leu-Arg-(HClO$_4$)-Asp(OBu$^t$)-Ser(Bu$^t$)-Ala-Arg(HClO$_4$)-Leu-Gln-Arg(HClO$_4$)

with the addition of 3-hydroxy-4-oxo-3,4-dihydro-1,2,3-benzotriazine with the appropriate peptides with free carboxyl groups in polar solvents with dicyclohexylcarbodiimide and the necessary amounts of a tertiary base, and precipitation of the peptides, which have thus been synthesized, as perchlorates from water with the addition of appropriate amounts of perchloric acid and, where appropriate, of a perchlorate.

8. The process as claimed in claim 7, wherein the peptide of the general formula (IIa) is obtained by hydrogenation of benzyloxycarbonyl-containing fragments of the general formula II $$Z\text{-}X\text{-}Leu\text{-}Leu\text{-}Gln\text{-}Leu\text{-}Val\text{-}NH_2 \qquad (II)$$

wherein X denotes
Arg($Z_2$)
-Arg($Z_2$)-Leu-Gln-Arg($HClO_4$)
-Arg($Z_2$)-Asp($OBu^t$)-Ser($Bu^t$)-Ala-Arg($HClO_4$)-Leu-Gln-Arg($HClO_4$)-or
-Thr($Bu^t$)-Ser($Bu^t$)-Glu($PBu^t$)-Leu-Ser-($Bu^t$)-Leu-Ser ($Bu^t$)-Arg($HClO_4$)-Leu-Arg($HClO_4$)-Asp($OBu^t$)-Ser ($Bu^t$)-Ala-Arg-($HClO_4$)-Leu-Gln-Arg($HClO_4$)- in dimethylacetamide with the addition of a palladium catalyst, the pH being maintained between 4 and 6 by addition of a solution containing perchloric acid, and is reacted further as claimed in claim 7.

9. The process as claimed in claim 1, wherein pyridinium perchlorate is used for the preparation of the perchlorate of the arginine-containing fragment.

* * * * *